(12) United States Patent
Tao et al.

(10) Patent No.: US 11,963,771 B2
(45) Date of Patent: Apr. 23, 2024

(54) AUTOMATIC DEPRESSION DETECTION METHOD BASED ON AUDIO-VIDEO

(71) Applicant: INSTITUTE OF AUTOMATION, CHINESE ACADEMY OF SCIENCES, Beijing (CN)

(72) Inventors: Jianhua Tao, Beijing (CN); Cong Cai, Beijing (CN); Bin Liu, Beijing (CN); Mingyue Niu, Beijing (CN)

(73) Assignee: INSTITUTE OF AUTOMATION, CHINESE ACADEMY OF SCIENCES, Beijing (CN)

( * ) Notice: Subject to any disclaimer, the term of this patent is extended or adjusted under 35 U.S.C. 154(b) by 476 days.

(21) Appl. No.: 17/472,191

(22) Filed: Sep. 10, 2021

(65) Prior Publication Data
US 2022/0265184 A1 Aug. 25, 2022

(30) Foreign Application Priority Data
Feb. 19, 2021 (CN) .......................... 202110188624.0

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/4803* (2013.01); *A61B 5/7275* (2013.01);
(Continued)

(58) Field of Classification Search
None
See application file for complete search history.

(56) References Cited

U.S. PATENT DOCUMENTS 11,232,290 B2 * 1/2022 McDuff ................. G16H 50/30
2019/0341025 A1 11/2019 Omote et al.
(Continued)

FOREIGN PATENT DOCUMENTS

CN 108647255 A 10/2018
CN 109171769 A 1/2019
(Continued)

OTHER PUBLICATIONS

Yan et al., Hybrid depression classification and estimation from audio video and text information, AVEC'17, (Year: 2017).*
(Continued)

*Primary Examiner* — Mohammed Rachedine
(74) *Attorney, Agent, or Firm* — Oliff PLC

(57) ABSTRACT

Disclosed is an automatic depression detection method using audio-video, including: acquiring original data containing two modalities of long-term audio file and long-term video file from an audio-video file; dividing the long-term audio file into several audio segments, and meanwhile dividing the long-term video file into a plurality of video segments; inputting each audio segment/each video segment into an audio feature extraction network/a video feature extraction network to obtain in-depth audio features/in-depth video features; calculating the in-depth audio features and the in-depth video features by using multi-head attention mechanism so as to obtain attention audio features and attention video features; aggregating the attention audio features and the attention video features into audio-video features; and inputting the audio-video features into a decision network to predict a depression level of an individual in the audio-video file.

10 Claims, 3 Drawing Sheets

(51) Int. Cl.

| | |
|---|---|
| *G06F 18/25* | (2023.01) |
| *G06N 3/044* | (2023.01) |
| *G06N 3/045* | (2023.01) |
| *G06N 3/048* | (2023.01) |
| *G06N 3/08* | (2023.01) |
| *G06T 7/00* | (2017.01) |
| *G06V 10/80* | (2022.01) |
| *G06V 20/40* | (2022.01) |
| *G10L 25/30* | (2013.01) |
| *G10L 25/57* | (2013.01) |
| *G10L 25/63* | (2013.01) |
| *G10L 25/66* | (2013.01) |

(52) U.S. Cl.
CPC ............ *G06F 18/253* (2023.01); *G06N 3/08* (2013.01); *G06T 7/0012* (2013.01); *G06V 20/46* (2022.01); *G06V 20/49* (2022.01); *G10L 25/30* (2013.01); *G10L 25/57* (2013.01); *G10L 25/63* (2013.01); *G10L 25/66* (2013.01); *G06T 2207/10016* (2013.01)

(56) References Cited

U.S. PATENT DOCUMENTS

2021/0133509 A1* 5/2021 Wall .......................... A61B 5/16
2021/0150215 A1* 5/2021 Zhang ...................... G10L 25/63
2022/0211774 A1* 7/2022 Patterson ................. A61P 25/22
2022/0230632 A1* 7/2022 Maitra ................. A61B 5/7267

FOREIGN PATENT DOCUMENTS

| CN | 109635791 A | | 4/2019 | |
|---|---|---|---|---|
| CN | 109919295 A | | 6/2019 | |
| CN | 110334243 A | | 10/2019 | |
| CN | 110556129 A | | 12/2019 | |
| CN | 110569869 A | | 12/2019 | |
| CN | 111243575 A | | 6/2020 | |
| CN | 111275085 A | | 6/2020 | |
| CN | 111429948 A | | 7/2020 | |
| CN | 111444382 A | | 7/2020 | |
| CN | 111680541 A | * | 9/2020 | ............. G06F 40/30 |
| CN | 111680541 A | | 9/2020 | |
| CN | 111723239 A | | 9/2020 | |
| CN | 111914734 A | | 11/2020 | |
| CN | 112331337 A | | 2/2021 | |

OTHER PUBLICATIONS

Apr. 6, 2021 Office Action issued in Chinese Patent Application No. 202110188624.0.

May 8, 2021 Office Action issued in Chinese Patent Application No. 202110188624.0.

May 28, 2021 Notice of Allowance issued in Chinese Patent Application No. 202110188624.0.

\* cited by examiner

AUTOMATIC DEPRESSION DETECTION METHOD BASED ON AUDIO-VIDEO

CROSS-REFERENCE TO RELATED APPLICATION

The present disclosure claims the priority to the Chinese Patent Application CN202110188624.0 entitled "End-to-end automatic depression detection and research method based on audio-video" filed on Mar. 26, 2021, the entire content of which is incorporated herein by reference.

FIELD OF THE INVENTION

The present disclosure relates to the fields of voice processing and image processing, and in particular to an automatic depression detection method using audio-video, and a computer-readable storage media and terminal device for the same.

BACKGROUND OF THE INVENTION

Depression is a mental illness that makes a person feels depressed and unable to participate in social life normally. Severe depression may lead to self-harm and suicidal behavior. Early diagnosis and treatment of depression can help patients get rid of the predicament as soon as possible. However, a process of diagnosing the depression is usually laborious and mainly depends on clinical experience of a doctor, resulting in that some patients cannot get proper treatment in time. Therefore, it is necessary to develop a method for automatically diagnosing depression so as to provide doctors with scientific and referable diagnosis conclusions.

In some existing solutions, machine equipment is given an ability of capturing potential clues of depression symptoms through an exploration on patterns of changes in terms of voice and face of healthy individuals against depression patients and designs of a corresponding model and method, so that the machine equipment's diagnostic capability is enhanced and diagnosis efficiency is improved.

However, these solutions usually use multiple steps and multiple models to carry out a prediction. As a result, not only does an object function of each template deviate from a final prediction target, but also errors are accumulated easily, resulting in low accuracy of the prediction result.

Patent application publication No. CN109171769A discloses a method and system for extracting voice features and facial features for depression detection. Audio data is subjected to feature extraction according to an energy information method, to obtain spectral parameters and acoustic parameters; these parameters are input into a first deep neural network model to obtain voice in-depth feature data; then, video images are subjected to static feature extraction to obtain frame images; the frame images are input into a second deep neural network model to obtain facial feature data; the video images are then subjected to dynamic feature extraction to obtain optical flow images; the optical flow images are input into a third deep neural network model to obtain facial motion feature data; and the facial feature data and the motion feature data are input into the third deep neural network model to obtain facial in-depth feature data; the voice in-depth feature data and the facial in-depth feature data are both input into a fourth neural network model to obtain fusion data. Patent application publication No. CN110556129A provides a bi-modal emotion recognition model training method and a bi-modal emotion recognition method, wherein the bi-modal emotion recognition model training method includes: inputting voice training data into a first neural network model for training to obtain a voice emotion recognition model; inputting image training data into a second neural network model, and using a first loss function to perform a first stage of supervised training so as to obtain a first stage of initial image emotion recognition model; inputting the image train data into the first stage of initial image emotion recognition model, using a second loss function to perform a second stage of supervised training so as to obtain a target image emotion recognition model, and performing decision-level fusion on the voice emotion recognition model and the target image emotion recognition model to obtain a bi-modal emotion recognition model.

SUMMARY OF THE INVENTION

In order to solve the above technical problems or at least partially solve these technical problems, the present disclosure provides an automatic depression detection method using audio-video, including steps of:

S1, acquiring original data containing two modalities of long-term audio file and long-term video file from an audio-video file;

S2, sampling the long-term audio file at a certain sampling rate and dividing the long-term audio file into several audio segments, and meanwhile sampling the long-term video file at a certain sampling rate and dividing the long-term video file into a plurality of video segments;

S3, inputting each audio segment into an audio feature extraction network to obtain in-depth audio features, the audio feature extraction network including an expanded convolution layer and a time sequence pooling layer; and inputting each video segment into a video feature extraction network to obtain in-depth video features, the video feature extraction network including a 3D convolution layer and a bidirectional long short-term memory network module;

S4, calculating the in-depth audio features and the in-depth video features by means of multi-head attention mechanism so as to obtain attention audio features and attention video features;

S5, aggregating the attention audio features and the attention video features into audio-video features through a feature aggregation model; and S6, inputting the audio-video features into a decision network to predict a depression level of an individual in the audio-video file.

In some exemplary embodiments of the present invention, the long-term audio file is sampled at a certain sampling rate, and is divided into several audio segments with a fixed length, wherein the audio segments are saved in a mat file format, where a label to which an original MP4 audio-video file corresponds is exactly a label of the mat file.

In some exemplary embodiments of the present disclosure, the long-term video file is sampled at a certain sampling rate and is divided into a plurality of video segments with a fixed number of frames, wherein a sequence of extracted video frames is saved in a jpg format, and a label that an original MP4 audio-video file corresponds to is exactly that of the jpg file.

In some exemplary embodiments of the present disclosure, inputting each audio segment into an audio feature extraction network to obtain in-depth audio features includes: performing, firstly, convolution expanding on an input audio by three times, wherein the number of convolution kernels is set to 256, a size of convolution kernel is set to 2, an expansion rate is set to 2, the number of convolution layers is set to 4, the number of input channels is 1, the number of output channels is 256, and a data length is of 256; then, performing down-sampling through the time sequence pooling layer to set the number of channels and a data length to 128, respectively, so that the in-deep audio features contain time sequence dynamic information.

In some exemplary embodiments of the present disclosure, inputting each video segment into a video feature extraction network to obtain in-depth video features includes: performing, firstly, 3D convolution on an input video frame, wherein the number of convolution kernels is set to 8, a size of convolution kernel is set to 3×3×3, and a step length is set to (2, 2, 2); then, inputting an output of the 3D convolution layer to the bidirectional long short-term memory network having the number of 64 output nodes to capture a time sequence representation of the video.

In some exemplary embodiments of the present disclosure, calculating the in-depth audio features and the in-depth video features by means of multi-head attention mechanism so as to obtain attention audio features and attention video features specifically includes: inputting the in-depth audio features and in-depth video features, respectively, into a multi-head attention module to obtain in-depth audio feature representations with varied weight distribution and in-depth video feature representations with varied weight distribution; and normalizing the in-depth audio feature representations with varied weight distribution and the in-depth video feature representations with varied weight distribution by means of a softmax function to obtain valued degrees with respect to different features as well as the attention audio features and the attention video features.

In some exemplary embodiments of the present disclosure, an attention formula of the multi-head attention module is, $$\text{Attention}(Q,K,V)=\text{soft max}(QK^T/\sqrt{d_k})V$$

where Q, K, V represent sets of input queries, keys and values, respectively, $d_k$ is the number of dimensions of Q and K, formulas of them are, respectively, $$Q=W_qX; K=W_kX; V=W_vX$$

where X is an input variable, $W_q$, $W_k$ and $W_v$ are matrices corresponding to Q, K and V, respectively.

In some exemplary embodiments of the present disclosure, the feature aggregation model includes a feedforward neural network.

In some exemplary embodiments of the present disclosure, the decision network adopts Dense Net.

In some exemplary embodiments of the present disclosure, the Dense Net is composed of Dense Blocks, wherein an input of each layer of a Dense Block comes from outputs of all the previous layers, and each layer directly obtains gradient from a loss function and an original input signal, so that implicit deep supervision can be implemented. Formula of the Dense Block is, $$X_l = H_l([X_0, X_1, \ldots, X_{l-1}])$$

where $H_l$ represents a nonlinear transformation, and $[X_0, X_1, \ldots, X_{l-1}]$ represents mapping of outputs from layer 0 to layer l-1.

On a further respect, an embodiment of the present disclosure further provides a computer-readable storage medium storing a computer program thereon, characterized in that, the computer program, when being executed by a processor, carries out the above-mentioned automatic depression detection method using audio-video.

On a yet respect, an embodiment of the present disclosure further provides a terminal device including a memory and a processor, wherein the memory stores a computer program there on, characterized in that, the computer program, when being executed by the processor, carries out the above-mentioned automatic depression detection method using audio-video.

The foregoing technical solutions provided by the embodiments of the present application have advantages as following.

In the methods provided in the embodiments of the disclosure, (1) neural networks are employed for automatic learning, which is beneficial to representation of in-depth features of depression detection, which eliminates manual extraction of features in the past, and implements an end (such as, audio-video equipment or a terminal device storing audio-video) to an end (i.e., a terminal device for depression detection) detection. The result indicates that features extracted by the neural networks can well reflect characteristics of a depressed individual and accuracy of automatic depression detection can be improved;

(2) taking into account the nature of time sequence of audio features and video features in the process of depression detection, the expanded convolution and the time sequence pooling, the 3D convolution and the bidirectional long short-term memory network are used to extract the audio features and the video features, respectively, and information of time sequence in audios and videos is obtained, and deeper features are extracted, so that a final depression detection result is more accurate.

BRIEF DESCRIPTION OF THE DRAWINGS

The drawings here are incorporated into the specification and constitute a part of the specification, which illustrate embodiments in accordance with the present disclosure and is applicable to explain the principle of the present disclosure together with the specification.

In order to more clearly describe the technical solutions in the embodiments of the present disclosure or the existing solutions in the art, accompanying drawings needed in the description of the embodiments or the existing solutions will be briefly introduced below. Apparently, for those of ordinary skill in the art, other drawings can be obtained based on these drawings without any inventive labor involved.

DETAILED DESCRIPTION OF THE EMBODIMENTS

In order to make purposes, technical solutions and advantages of the embodiments of the present disclosure more definite, the technical solutions of the embodiments of the present disclosure will be described clearly and completely below in conjunction with accompanying drawings. Apparently, the embodiments described herein merely constitute a portion, rather than the whole, of the embodiments of the present disclosure. On the basis of the embodiments of the present disclosure, all other embodiments obtained by those of ordinary skill without any inventive labor involved should fall within the protection scope of the present disclosure.

Figure 1:
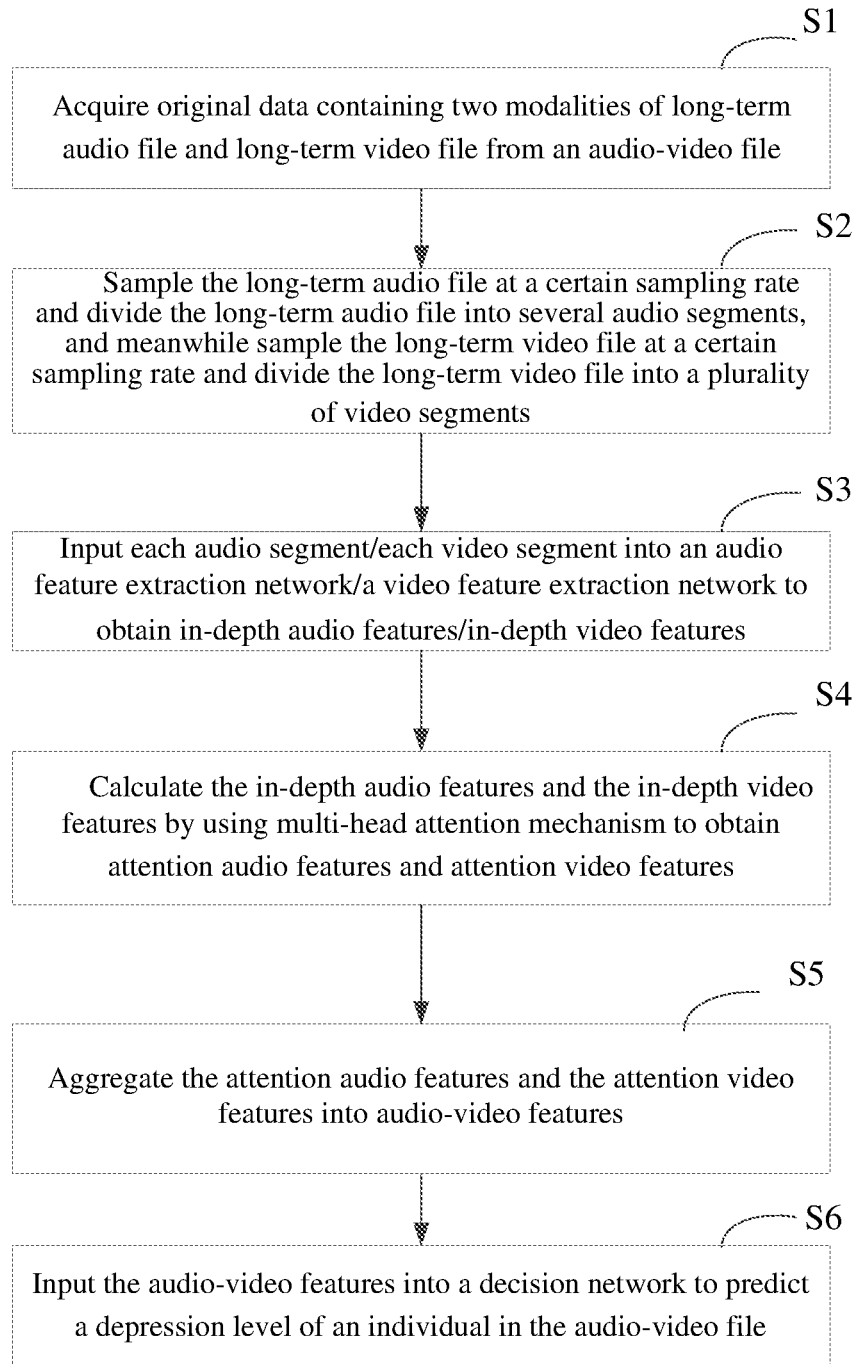
FIG. 1 is a flowchart of an automatic depression detection method using audio-video according to an embodiment of the disclosure.
Figure 2:
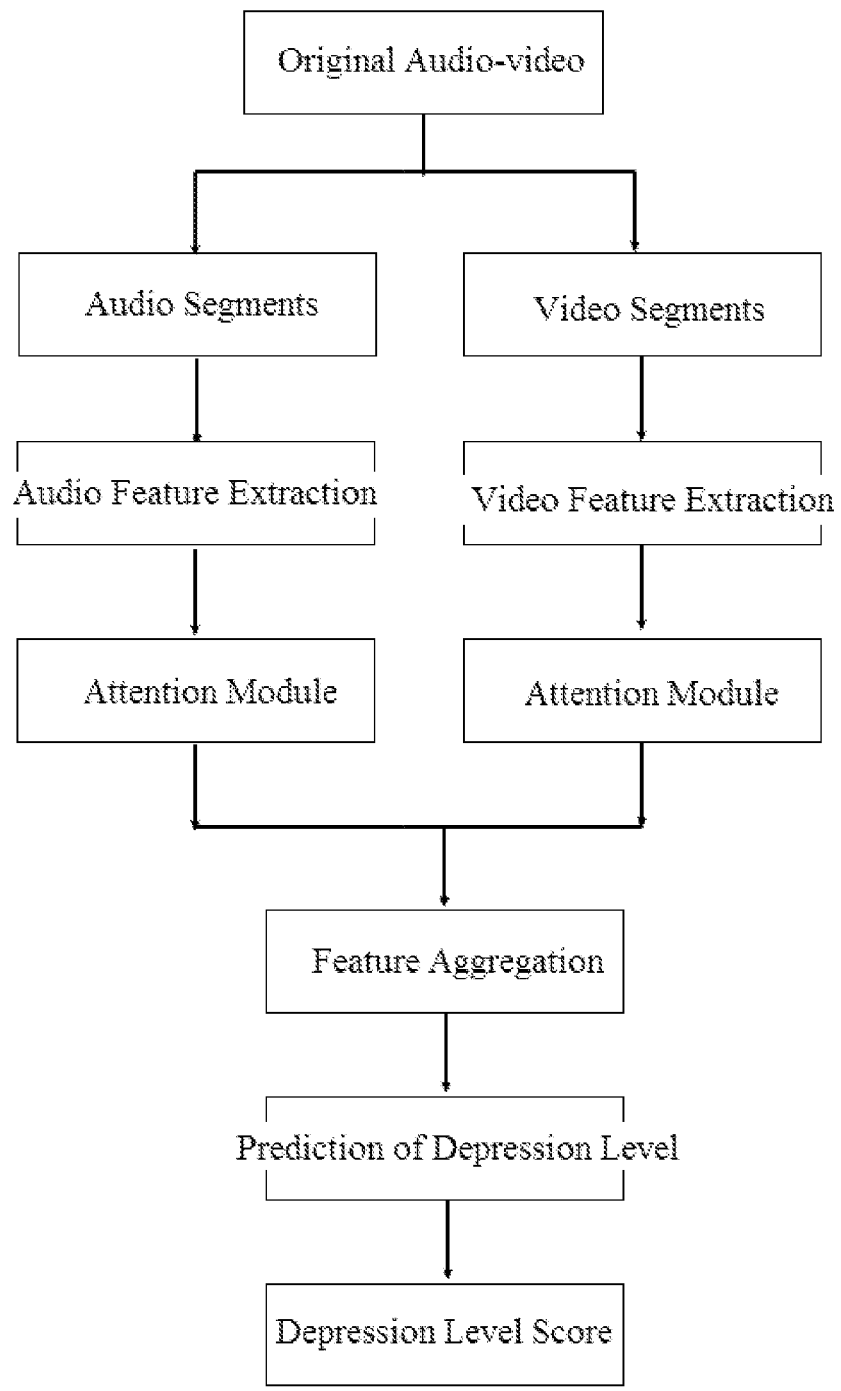
FIG. 2 is a structural diagram showing an automatic depression detection method using audio-video according to an exemplary embodiment of the disclosure.

As shown in FIGS. 1 and 2, an automatic depression detection method using audio-video includes steps S1 to S6.

In step S1, original data containing two modalities of long-term audio file and long-term video file are acquired from an audio-video file.

In step S2, the audio-video file is pre-processed.

The long-term audio file is sampled at a certain sampling rate to obtain original waveform points of the long-term audio file, and is divided into several audio segments with a fixed length. In this embodiment, the audio segments are saved in a mat file format, where a label to which an original MP4 audio-video file corresponds is exactly the label of the mat file.

The long-term video file is sampled at a certain sampling rate, and is divided into a plurality of video segments with a fixed number of frames. In this embodiment, an extracted video frame sequence is saved in a jpg format, where a label that an original MP4 audio-video file corresponds to is exactly that of the jpg file.

In step S3, each audio segment/each video segment is input into an audio feature extraction network/a video feature extraction network to obtain in-depth audio features/in-depth video features.

In this embodiment, the audio feature extraction network includes an expanded convolution layer and a time sequence pooling layer; and the video feature extraction network includes a 3D convolution layer and a bidirectional long short-term memory network module.

Expanded convolution may ensure that extraction of features does not violate an order of data, and has a larger receptive field than convolution, where the receptive field increases in an exponential manner along with the increase in an expansion factor. Time sequence pooling takes into account a temporal relationship of features can capture crucial features in a time sequence, and can enable down-sampling and decrease a size of parameter.

In step S4, multi-head attention mechanism is employed for calculation of the in-depth audio features and the in-depth video features so as to obtain attention audio features and attention video features; the in-depth audio features and the in-depth video features are input into a multi-head attention module, respectively, to obtain in-depth audio feature representations with varied weight distribution and in-depth video feature representations with varied weight distribution.

The in-depth audio feature representations with varied weight distribution and the in-depth video feature representations with varied weight distribution are normalized by means of a softmax function to obtain valued degrees with respect to different features, so that the attention audio features and the attention video features are obtained.

Wherein, an attention formula of the multi-head attention module is, $$\text{Attention}(Q,K,V)=\text{soft max}(QK^T/\sqrt{d_k})V$$

where Q, K, V represent sets of input queries, keys and values, respectively, $d_k$ is the number of dimensions of Q and K, formulas of them are, respectively, $$Q=W_q X; K=W_k X; V=W_v X$$

where X is an input variable, $W_q$, $W_k$ and $W_v$ are matrices corresponding to Q, K and V, respectively.

In step S5, the attention audio features and the attention video features are aggregated into audio-video features by means of a feature aggregation model. In this embodiment, the feature aggregation model includes a feedforward neural network.

In step S6, the audio-video features are input into a decision network so that a depression level of an individual in the audio-video file can be predicted. In this embodiment, the decision network adopts Dense Net; the Dense Net is composed of Dense Blocks. An input of each layer of a Dense Block comes from outputs of all the previous layers and each layer can directly obtain the gradient from a loss function and an original input signal so that implicit deep supervision can be implemented. Formula of the Dense Block is, $$X_l = H_l([X_0, X_1, \ldots, X_{l-1}])$$

where $H_l$ represents a nonlinear transformation, and $[X_0, X_1, \ldots, X_{l-1}]$ represents mapping of outputs from layer 0 to layer l−1.

Therefore, on the premise of ensuring the maximum information transmission between layers in the network, the Dense Net directly connects all layers so that not only does it exceed Res Net in accuracy, but also greatly reduces the amount of parameters and calculations, and also has better generalization.

Specific Embodiments

Inputting audio-video file: depression detection data set in the year 2013 (AVEC 2013) is downloaded from an official website of Audio Video Motion Challenge. The AVEC 2013 is a subset of an audiovisual depression corpus, and is recorded through a webcam and microphone with a total 150 videos from 82 subjects. These videos are divided into three parts: train, dev, and test, each part having 50 samples, each video being of 30 frames per second and a resolution of 640×480, and each sample being labeled with BDI-II score.

Audio-video preprocessing: audios are extracted from an original video of the downloaded AVEC 2013 data set by using a FFMPEG tool and saved in a way format. A long-term audio is divided into audio files of 3 s, and then sampled at a sampling rate of 8K Hz to obtain original waveform points of the audio, which are saved in a mat format and have labels that are exactly the ones of the original audio-video. Then, videos are obtained by sampling the original video at a rate of 6 times/s, and the obtained video frames are saved in a jpg format and have labels of that of the original audio-video.

Extraction of audio features and video features: the audio files and the video files are input, respectively, into an audio feature extraction network and a video feature extraction network:

The audio feature extraction network consists of expanded convolution and time sequence pooling. First, an input audio is subjected to convolution expanding by three times, where the number of convolution kernels is set to 256, a size of convolution kernel is set to 2, an expansion rate is set to 2, the number of convolution layers is set to 4, the number of input channels is 1, and the number of output channels is 256. Then, down-sampling is performed through the time sequence pooling layer, where the number of channels and a data length are set to 128, respectively. At this time, the audio features contain time sequence dynamic information so that the extracted features are more robust, which are more advanced;

The video feature extraction network consists of a 3D convolution and a bidirectional long short-term memory network. First, an input video frame is subject to 3D convolution, wherein the number of convolution kernels is set to 8, a size of convolution kernel is set to 3×3×3, and a step length is set to (2, 2, 2); Then, video features are input into the bidirectional long short-term memory network having the number of 64 output nodes so that a time sequence representation of the video is captured.

In this way, through the feature extraction networks, in-depth feature representation of the audio (i.e., in-depth audio features) and in-depth feature representation of the video (i.e., in-depth video features) are obtained, respectively;

Extraction of attention features: the in-depth audio features and in-depth video features, respectively, are input into a multi-head attention module to obtain in-depth feature representations with varied weight distribution. In this embodiment, the number of attention heads is set to 8, which means that similarity between hidden layer representation of a feature and the feature itself is calculated from eight perspectives, and then normalization is performed by means of a softmax function to obtain valued degrees of different features as well as attention audio features and attention video features.

Aggregation of audio and video features: the attention audio features and the attention video features are aggregated into audio-video features through a feature aggregation model. In this embodiment, the audio features and the video features may be directly spliced together to form the audio-video features including features of the two modalities of audio and video and also features of interaction of the two modalities.

Depression level detection: the aggregated audio-video feature representations are input into a decision network to predict a depression level of an individual in the input audio-video file. In this embodiment, the decision network adopts Dense Net, where a growth rate is set to 16, the number of Dense Blocks is 4, convolution operations in a Dense Block are performed for (6, 12, 24, 16) times. Finally, a result thereof is input into a fully connected layer, and the number of output nodes is 1, which represents a score of the depression level of the input individual.

On the basis of the foregoing embodiments, an embodiment of the present disclosure provides a readable storage medium characterized in that the readable storage medium stores one or more programs, which may be executed by one or more processors to implement the automatic depression detection method using audio-video as described in the foregoing embodiments.

Optionally, the aforementioned storage medium may be a non-transitory computer-readable storage medium. For example, the non-transitory computer-readable storage medium may be ROM, random access memory (RAM), CD-ROM, magnetic tape, floppy disk, and optical data storage device, etc.

Figure 3:
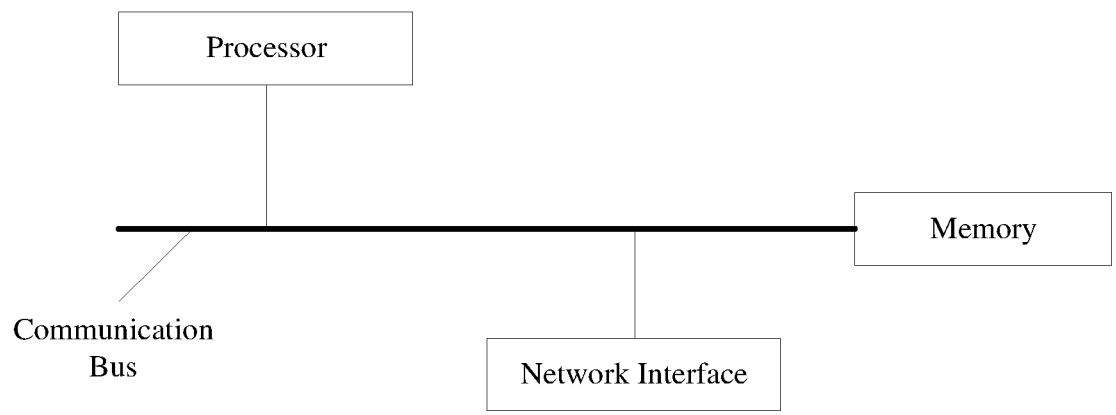
FIG. 3 is a schematic diagram showing composition structure of a terminal device according to an exemplary embodiment of the disclosure.

In addition, as shown in FIG. 3, another embodiment of the present disclosure further provides a terminal device, including a processor and a memory;
the memory is configured to store a computer program;
the processor is configured to execute the computer program stored in the memory to implement the automatic depression detection method using audio-video as described in the foregoing embodiments.

The aforementioned processor may be a general-purpose processor, including a Central Processing Unit (CPU), a Network Processor (NP), etc. It may also be a Digital Signal Processor (DSP), Application Specific Integrated Circuit (ASIC), Field-Programmable Gate Array (FPGA) or other programmable logic devices, discrete gates or transistor logic devices, discrete hardware components.

It should be noted that, in this document, relational terms such as "first" and "second" are merely used to distinguish one entity or operation from another entity or operation, and do not intent to require or imply any such actual relationship or sequence between these entities or operations. Moreover, wordings "include", "comprise" or any other variants thereof are intended to cover non-exclusive inclusion, so that a process, method, article or device including a series of elements not only includes those elements, but also include other elements that have not been listed definitely or elements inherent to the process, method, article, or device. Except that there is further limitation, an element defined by the wordings, such as "include a . . . " does not exclude existence of other identical elements included in the process, method, article, or device including said element.

These above are only specific embodiments of the present disclosure to facilitate understanding or implementation of the present disclosure by those skilled in the art. Various modifications to these embodiments will be apparent to those skilled in the art, and the general principles defined herein can be implemented in other embodiments without departing from the spirit or scope of the present disclosure. Therefore, the present disclosure will not be limited to the embodiments illustrated in this document, but should conform to the broadest scope consistent with the principles and novel features provided in this document.

What is claimed is:

1. An automatic depression detection method using audio-video, characterized in that, the method comprises steps of:

S1, acquiring original data containing two modalities of long-term audio file and long-term video file from an audio-video file;

S2, sampling the long-term audio file at a certain sampling rate and dividing the long-term audio file into several audio segments, and meanwhile sampling the long-term video file at a certain sampling rate and dividing the long-term video file into a plurality of video segments;

S3, inputting each audio segment into an audio feature extraction network to obtain in-depth audio features, the audio feature extraction network comprising an expanded convolution layer and a time sequence pooling layer;

wherein inputting each audio segment into an audio feature extraction network to obtain in-depth audio features comprises: performing, firstly, convolution expanding on an input audio by three times, wherein a quantity of convolution kernels is set to 256, a size of convolution kernel is set to 2, an expansion rate is set to 2, a quantity of convolution layers is set to 4, a quantity of input channels is 1, a quantity of output channels is 256, and a data length is of 256; then, performing down-sampling through the time sequence pooling layer, wherein a quantity of channels and a data length are set to 128, respectively, so that the in-deep audio features contain time sequence dynamic information; and inputting each video segment into a video feature extraction network to obtain in-depth video features, the video feature extraction network comprising a 3D convolution layer and a bidirectional long short-term memory network module;
wherein inputting each video segment into a video feature extraction network to obtain in-depth video features comprises: performing, firstly, 3D convolution on an input video frame, wherein a quantity of convolution kernels is set to 8, a size of convolution kernel is set to 3×3×3, and a step length is set to (2, 2, 2); then, inputting an output of the 3D convolution layer to the bidirectional long short-term memory network having a quantity of 64 output nodes to capture a time sequence representation of the video;

S4, calculating the in-depth audio features and the in-depth video features by using multi-head attention mechanism so as to obtain attention audio features and attention video features;

S5, aggregating the attention audio features and the attention video features into audio-video features through a feature aggregation model; and S6, inputting the audio-video features into a decision network to predict a depression level of an individual in the audio-video file.

2. The method according to claim 1, wherein the long-term audio file is sampled at a certain sampling rate and is divided into several audio segments with a fixed length, wherein the audio segments are saved in a mat file format, and a label to which an original MP4 audio-video file corresponds is a label of the mat file.

3. The method according to claim 2, wherein the long-term video file is sampled at a certain sampling rate and is divided into a plurality of video segments with a fixed number of frames, wherein a sequence of extracted video frames is saved in a jpg format, and a label to which an original MP4 audio-video file corresponds is a label of the jpg file.

4. The method according to claim 1, wherein calculating the in-depth audio features and the in-depth video features by using multi-head attention mechanism so as to obtain attention audio features and attention video features includes:
inputting the in-depth audio features and in-depth video features, respectively, into a multi-head attention module to obtain in-depth audio feature representations with varied weight distribution and in-depth video feature representations with varied weight distribution; and normalizing the in-depth audio feature representations with varied weight distribution and the in-depth video feature representations with varied weight distribution by using a softmax function to obtain valued degrees with respect to different features, and the attention audio features and the attention video features.

5. The method according to claim 4, wherein an attention formula of the multi-head attention module is, $$\text{Attention}(Q,K,V)=\text{soft max}(QK^T/\sqrt{d_k})V$$

where Q, K, V represent sets of input queries, keys and values, respectively, $d_k$ is dimensions of Q or K, formulas of them are, respectively, $$Q=W_qX; K=W_kX; V=W_vX$$

where X is an input variable, $W_q$, $W_k$ and $W_v$ are matrices corresponding to Q, K and V, respectively.

6. The method according to claim 1, wherein the feature aggregation model includes a feedforward neural network.

7. The method according to claim 1, wherein the decision network adopts Dense Net.

8. The method according to claim 7, wherein the Dense Net consists of Dense Blocks, wherein an input of each layer of a Dense Block comes from outputs of all the previous layers, and each layer obtains gradient from a loss function and an original input signal, so that implicit deep supervision can be implemented, and wherein a formula of the Dense Block is, $$X_l=H_l([X_0,X_1,\ldots,X_{l-1}])$$

where $H_l$ represents a nonlinear transformation, and $[X_0, X_1, \ldots, X_{l-1}]$ represents mapping of outputs from layer 0 to layer l−1.

9. A computer-readable storage medium storing a computer program thereon, wherein the computer program, when being executed by a processor, carries out the automatic depression detection method using audio-video according to claim 1.

10. A terminal device comprising a memory and a processor, wherein the memory storing a computer program there on, characterized in that, the computer program, when being executed by the processor, carries out the automatic depression detection method using audio-video according to claim 1.

* * * * *